United States Patent [19]

Cross

[11] Patent Number: 4,889,732

[45] Date of Patent: Dec. 26, 1989

[54] METHOD FOR TREATING HAYS, GRAINS & SILAGES

[75] Inventor: Dee L. Cross, Central, S.C.

[73] Assignee: Clemson University, Clemson, S.C.

[21] Appl. No.: 247,907

[22] Filed: Sep. 22, 1988

[51] Int. Cl.$^4$ .............................................. A23B 9/00
[52] U.S. Cl. .................................. 426/319; 426/640; 426/807; 562/555
[58] Field of Search ............... 426/52, 640, 319, 807; 562/555

[56] References Cited

U.S. PATENT DOCUMENTS

| | | | |
|---|---|---|---|
| 4,199,606 | 4/1980 | Bland | 426/331 |
| 4,426,396 | 1/1984 | Young | 426/69 |
| 4,540,586 | 9/1985 | Moore | 426/69 |
| 4,549,960 | 10/1985 | Hoppe | 426/320 |

OTHER PUBLICATIONS

Gove, P., Webster's Third New International Dictionary, 1961, G.& C. Merriam Co., Publishers, Springfield, Mass., p. 2276.

Hawley, 10th Ed., The Condensed Chemical Dictionary, 1981, Van Nostrand Reinhold Co., p. 58.

Cross et al., "Effect of Ammonium Carbamate on Nutritive, Preservative, and Digestibility Characteristics of High Moisture Coastal Bermudagrass Forage," abstract, Southern Section of the American Society of Animal Sciences, Feb. 1, 1988, New Orleans, LA.

Primary Examiner—Donald E. Czaja
Assistant Examiner—Helen Pratt
Attorney, Agent, or Firm—Dority & Manning

[57] ABSTRACT

A method of treating organic farm materials such as hays, grains, and silages confines same to a predetermined enclosure. A solid chemical mixture is introduced into the enclosure. The solid chemical mixture is a urea reactor product including ammonium carbamate, ammonia, urea, and water. Heat is applied to the mixture to thereby release sufficient gaseous ammonia to the organic farm material to prevent spoilage, reduce toxin levels, and improve fermentation of the organic farm material. The solid chemical mixture disposed amidst the organic farm material can be provided in a corrosion resistant drum having holes through the top thereof and having an electric resistance heater disposed in the bottom thereof or underneath same. A thermostatic control can control the temperature generated by the heater. The drum with the solid mixture is disposed in the midst of bales of organic farm material which has been covered by plastic sheeting weighted at the edges with mounded dirt to render the enclosure substantially gas-tight.

15 Claims, 2 Drawing Sheets

METHOD FOR TREATING HAYS, GRAINS & SILAGES

BACKGROUND OF INVENTION

This invention relates to a method for treating hays, grains, and silages, and more particularly an improved method for preventing microbial growth and spoilage of feedgrains and hays, for detoxifying aflatoxins in grains, and for increasing the lactic acid content in silages to improve their fermentation.

As of this writing, the United States Food and Drug Administration prevents interstate shipment of or use in animal feeds of grains containing more than 20 parts per billion (ppb) of aflatoxin $B_1$. Thus, if grain containing more than 20 ppb of aflatoxin $B_1$ could be detoxified to contain less than 20 ppb of aflatoxin $B_1$, then this grain could be put to productive use.

It is desireable to harvest hay with sufficient moisture to prevent leaf shattering during the harvesting. This is because much of the nutrient value of the hay is contained in the leaves, and the harvesting of dry hay results in the destruction and loss of the leaves during the harvesting process. However, storing large quantities (on the order of several tons) of high moisture hay (greater than 22% moisture by weight of the hay) normally results in heating and production of mold within two weeks after storage. The growth of this mold substantially reduces the feed value of the hay and can be toxic to livestock. Thus, a method of retarding the heating and mold formation of this type of high moisture forage is desireable.

Lactic acid production is generally accepted as an accurate measure of the success of the anaerobic fermentation process of silage. Thus, it is desireable to increase the degree of fermentation of silage. Such increase is evidenced by an increased lactic acid content.

Animal feeds such as grains, hays, and silages have been exposed to anhydrous gaseous ammonia for the purposes of controlling microbial growth and spoilage, detoxifying aflatoxins, and increasing fermentation in silages. Regarding the effect of gaseous anhydrous ammonia ($NH_3$) on dry and high moisture (HM) coastal Bermudagrass hay, see Cross et al., "Effect of Moisture Level and Injection of Ammonia on Nutrient Quality and Preservation of Coastal Bermudagrass Hay," Journal of Animal Science. Volume 61, No. 6, pages 1370–1377 (1985); and Cross et al., "Effect of Ammonia Level and Time of Exposure to Ammonia on Nutritional and Preservatory Characteristics of Dry and High-Moisture Coastal Bermudagrass Hay," Animal Feed Science and Technology, Elsevier Science Publishers B. V., Amsterdam, Volume 14, pages 55–65 (1986). It has been known prior to the invention that the exposure to gaseous ammonia can be effected within a substantially gas tight enclosure, such as a silo or a plastic sheeting. However, gaseous ammonia is both costly and dangerous to the farmers who must store and use it.

U.S. Pat. No. 4,426,396 to Young discloses a method for treating animal feed stuffs destined for storage. The Young method employs a solution of urea, ammonia, and urea polymers such as biuret, triuret, cyanuric acid, and urea cyanurate to effect a chemical release of gaseous ammonia over time. It is believed that the urease enzyme causes the urea polymers to decompose slowly. This gradual decomposition caused by the urease enzyme sustains the presence of ammonia for a period of time beyond the decomposition of the initially present urea. However, the urease enzyme is costly, and the rate at which ammonia is released cannot be reliably predicted.

OBJECTS AND SUMMARY OF THE INVENTION

One of the principal objects of the present invention is to provide a method and apparatus for increasing the fermentation of silage.

Another principal object of the present invention is to provide a method and apparatus for detoxifying grain to acceptable levels of aflatoxin $B_1$ content to enable the grain to be shipped interstate or reduce the level enough to be safely used in animal feed.

Still another principal object of the present invention is to provide an improved method and apparatus that inhibits the formation of mold in high moisture forage.

A further principal object of the present invention is to provide a method and apparatus for treating high moisture forage that results in accelerated weight gain of the animals eating the forage.

Yet another principal object of the present invention is to provide a method and apparatus for controlling the release of ammonia from a dry ammonia precursor that is advantageous for treating animal feeds such as grains, hays, and silages to prevent microbial growth and spoilage of same, for detoxification of aflatoxins in same and for improving fermentation of silages by increasing the lactic acid content of these silages.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the method for treating organic farm material such as hays, grains, and silages comprises the following steps. The organic farm material is confined to a predetermined enclosure. A solid chemical mixture is introduced into the enclosure. Heat is then applied to the solid chemical mixture to thereby release sufficient gaseous ammonia to the organic farm material to prevent spoilage, reduce toxin levels, and improve fermentation of the organic farm material.

Preferably, the predetermined enclosure is rendered substantially gas tight. For example, organic farm materials such as bales of hay can be covered with plastic sheeting which is anchored at the edges by weights such as mounding dirt thereon. In another embodiment, the organic farm material can be enclosed in a substantially gas-tight silo. In still another alternative embodiment, the organic farm material can be stored in a pit dug into the ground. The organic farm material near the opening of the pit is allowed to rot to cover the top of the organic material with viscous decaying matter that forms a substantially gas-tight cover for the underlying and non-decayed organic material. In still a further alternative embodiment, the organic material can be confined in a pit dug into the ground and covered with plastic sheeting anchored at the edges by weights such as mounting dirt thereon.

Preferably, the solid chemical mixture includes ammonium carbamate. In addition to ammonium carbamate, the solid chemical mixture can include ammonium hydroxide, urea, and water. A solid chemical mixture including 57% ammonium carbamate, 14% ammonium hydroxide 12% urea, and 17% water, all percentages by weight, is suitable for practicing the present invention.

In further accordance with the apparatus of the present invention, the solid chemical mixture is contained in a corrosion resistant container, such as a 55 gallon drum for example, and heating is provided by an electrical resistance device disposed in the bottom of the drum or underneath same. In a preferred embodiment of the present invention, a thermostatic temperature control is provided to regulate the electrical resistance heating device. A plurality of holes are provided through the top of the drum. The temperature control facilitates release of the ammonia to the organic farm material at a controlled release rate, which is a function of the duration of activation of the electrical resistance device and the temperature generated by the electrical resistance device.

In an alternative embodiment of the present invention, the predetermined enclosure for confining the organic farm material can include a silo. In another alternative embodiment of the present invention, the predetermined enclosure for confining the organic farm material can include a pit dug into the ground. In each of these latter two embodiments of the present invention, the solid chemical mixture can be introduced into the predetermined enclosure by sprinkling or dusting the solid chemical mixture onto the organic farm material as it is harvested in the field. Another way of introducing the solid chemical mixture into the silo is to meter granular chunks of it as the organic material is blown up into the silo. This involves blowing the dry solid chemical mixture into the silo along with the organic material.

The accompanying drawings, which are incorporated in and constitute a part of this specification, illustrate at least one preferred embodiment of the invention and, together with the description, serve to explain the principles of the invention.

DESCRIPTION OF THE PREFERRED EMBODIMENT

Reference will now be made in detail to the present preferred embodiments of the invention, examples of which are illustrated in the accompanying drawings.

In accordance with the present invention, the method for treating organic farm material such as hays, grains, and silages comprises the following steps. The organic farm material is confined to a predetermined enclosure. As embodied herein and shown for example in FIG. 1, organic farm materials such as bales 10 of hay can be covered with plastic sheeting 12. For example, the edges of the plastic sheeting covering the bales can be anchored by weights such as mounded dirt 14 thereon.

In an alternative embodiment of the present invention, the predetermined enclosure for confining the organic farm material can include a silo. In another alternative embodiment of the present invention, the predetermined enclosure for confining the organic farm material can include a pit dug into the ground.

Preferably, the predetermined enclosure is rendered substantially gas tight. In alternative embodiments, the organic material confined to the pit can be covered with plastic sheeting weighted at the edges with dirt mounded thereon, or the organic material near the top of the pit can be permitted to decay and form a substantially gas-tight viscous film on the top.

In accordance with the present invention, a solid chemical mixture is introduced into the enclosure. Preferably, the solid chemical mixture includes ammonium carbamate. In its pure form, ammonium carbamate is very expensive and very unstable. A source of ammonium carbamate harvested from a urea reactor was found to be relatively inexpensive and more stable than pure ammonium carbamate. The admixture constituting the Urea Reactor Product (URP) contained 57% ammonium carbamate, 14% ammonium hydroxide, 12% urea and 17% water (all percentages by weight). This URP admixture was supplied by Columbia Nitrogen of Augusta, Ga., and is the URP used in the Examples discussed hereinafter.

Thus, in addition to ammonium carbamate, the solid chemical mixture preferably includes ammonium hydroxide, urea, and water. A solid chemical mixture, including 57% ammonium carbamate, 14% ammonium hydroxide, 12% urea, and 17% water, all percentages by weight, is suitable for practicing the present invention.

Figure 1:
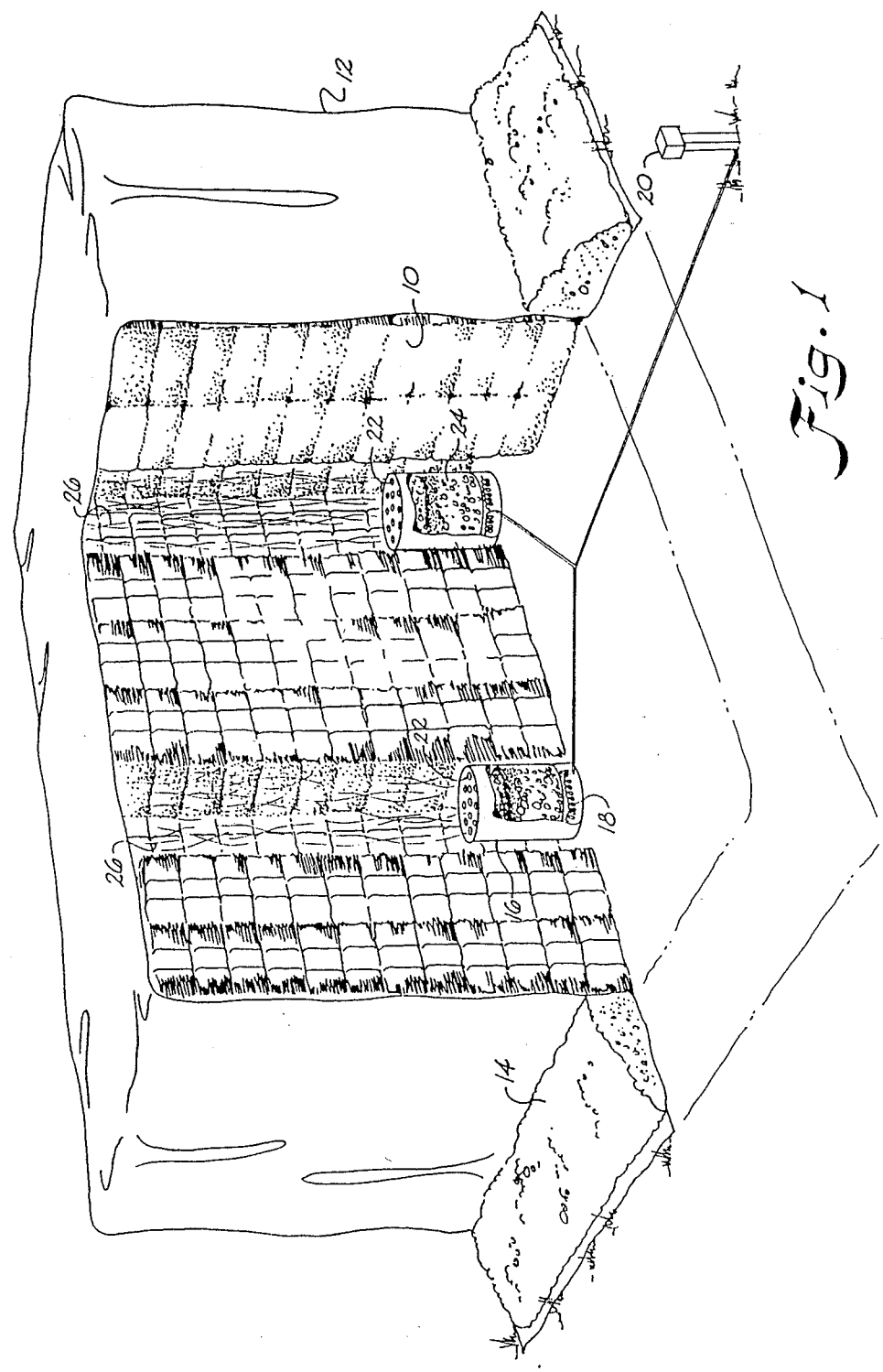
FIG. 1 illustrates a schematic perspective view of apparatus for practicing the present invention.

In accordance with the apparatus of the present invention, the solid chemical mixture is contained in a corrosion resistant container, such as a 55 gallon stainless steel drum 16 shown for example in FIG. 1. When the solid mixture is handled, it begins to turn partly to a liquid. The container should be airtight for shipping, but should be designed to allow for vapor release when in use. The drum has a plurality of holes 22 defined through the top thereof.

In each of the silo and pit embodiments of the present invention, the solid chemical mixture can be introduced into the predetermined enclosure by metering aggregates of the solid mixture into the organic farm material as the organic farm material is harvested in the field. Another way of introducing the solid chemical mixture into the silo is to meter aggregates of it as the organic material is blown up into the silo. This involves blowing the dry solid chemical mixture into the silo along with the organic material.

In further accordance with the method of the present invention, heat is then applied to the solid chemical mixture to thereby release sufficient gaseous ammonia to the organic farm material to prevent spoilage, reduce toxin levels, and improve fermentation of the organic farm material.

Figure 2:
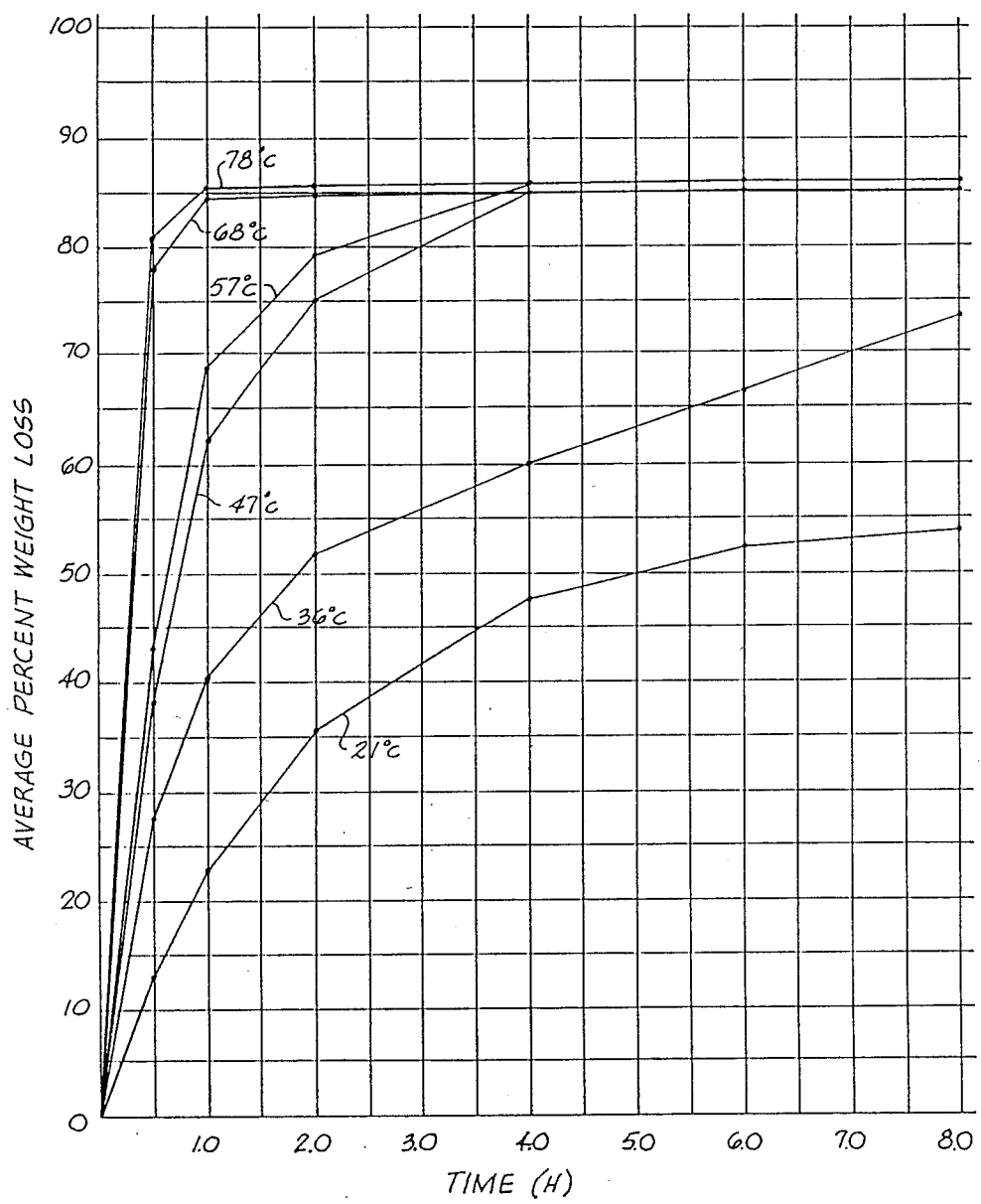
FIG. 2 illustrates a graphical presentation of the average percent weight loss of ammonium carbamate as a function of time at different temperatures.

In still further accordance with the method of the present invention, a time release method is provided for controlling the release rate of the vapors, and the time release mechanism is temperature regulated. The preferred temperature range is from 21° C. up to 60° C. The desired release rates are obtained by utilizing temperatures intermediate to these extremes. As shown in FIG. 2 for example, the higher release rates are obtained at the higher temperatures, and lower release rates at the lower temperatures.

Numerous approaches in design may be taken to accomplish the objective of controlled vapor release. In silage for example, temperature of fermentation will cause a slow release of ammonia without supplemental heat. If storage duration is indefinite, an excess of this chemical mixture can be placed in storage bins, silos or hay stacks, and ammonia released as required. However if a controlled, rapid release is desired, a supplemental heating device will be required. A thermostatically controlled heating device, preferably an electrical resistance device, should either be incorporated into the design of the container or the heating device designed to be added to the container. Thus, the release of the vapors and the amount of ammonia to be applied to the organic material will be controlled by the temperature setting on the thermostat and the volume of the chemical mixture placed in contact with the organic material.

As embodied herein and shown in FIG. 1 for example, heating is preferably provided by an electrical resistance device 18 disposed in the bottom of the drum or underneath same. In a preferred embodiment of the present invention, a thermostatic temperature control 20 is provided to regulate the electrical resistance heating device. This facilitates release of the ammonia to the organic farm material at a controlled release rate, which is a function of the duration of activation of the electrical resistance device and the temperature generated by the electrical resistance device.

As shown in FIG. 2, the average percent weight loss of a solid chemical mixture comprising 57% ammonium carbamate, 14% ammonium hydroxide, 12% urea, and 17% water, all percentages by weight, is represented graphically as a function of time at different temperatures, including 21° C., 36° C., 47° C., 57° C., 68° C., and 78° C. The numerical values of the plotted points are presented below in TABLE I, wherein each value is the mean of four observations.

TABLE I

NUMERICAL VALUES OF PLOTTED POINTS

| Time (h) | Average Percent Weight Loss of Admixture Temperatures (°C.)* | | | | | |
|---|---|---|---|---|---|---|
| | 21 | 36 | 47 | 57 | 68 | 78 |
| 0.50 | 13.11 | 17.62 | 38.28 | 42.93 | 77.99 | 80.90 |
| 1.00 | 22.90 | 40.07 | 62.22 | 68.72 | 84.67 | 85.65 |
| 2.00 | 35.35 | 51.88 | 75.08 | 84.06 | 84.80 | 85.80 |
| 4.00 | 47.46 | 60.26 | 85.04 | 85.57 | 84.91 | 85.89 |
| 6.00 | 52.48 | 66.74 | 85.63 | 85.58 | 85.02 | 86.04 |
| 8.00 | 54.09 | 73.76 | 85.67 | 85.60 | 85.02 | 86.07 |

*Each value is the mean of four observations.

As embodied herein and shown for example in FIG. 1, two 55-gallon steel drums are disposed in a hay stack. A plurality of holes 22 are formed through the top of each drum. An electrical resistance heater 18 is disposed underneath each drum. The heaters are connected to a thermostat to control the temperature of the solid chemical mixture 24 and therefore to control the release rate of the ammonia. The hay stack is covered with plastic sheeting to prevent loss of the ammonia vapors 26 which permeate and diffuse throughout the hay-stack.

Heating a URP admixture comprising 57% ammonium carbamate, 14% ammonium hydroxide, 12% urea and 17% water (all percentages by weight), in the presence of the animal feed, provided for a controlled release of ammonia which is advantageous for preventing heating and molding in grains and hays and to improve fermentation in silages.

This invention is useful for treating feed-grains and hays to prevent microbial growth and spoilage and for detoxification of aflatoxins in grains. Also, this invention is useful for improving the fermentation of silages by increasing the lactic acid content in silages. Control of microbial growth, detoxification of aflatoxins and increased fermentation in silages is due to release of ammonia vapors.

The ammonia treatment can be considered temporary, unless storage of the feed products is in a gas tight enclosure. Animal feeds usually are not stored in gas tight structures, therefore loss of ammonia vapors occurs. The temperature controlled, time release mechanism of the present invention allows for periodic release of ammonia vapors as required by the specific situation.

Further description of the invention is provided by means of the examples which follow.

EXAMPLE 1

The urea reactor product (URP) was applied to corn silage to determine its effect on silage fermentation. Lactic acid production is generally accepted as an accurate measure of the success of this anaerobic fermentation process. URP was applied at 1.5% of the weight of the silage. The silage was placed in sealed glass containers with added URP and maintained at 60° C. for 4 hours. It then was allowed to cool back to room temperature at its own rate. After 12 hours at room temperature, it then was heated to 55° C. and maintained at 55° C. for 2 hours. Subsequently, the containers were maintained at room temperature for four weeks, and aliquot samples removed and frozen for later analysis for lactic acid content. The increased lactic acid content with URP addition is shown in TABLE II. This demonstrates the advantage of this URP admixture product for increasing fermentation and therefore the preservation and feeding value of the silage. Also, the additional nitrogen added to the silage from the URP can be utilized by rumen microorganisms of cattle to synthesize usable protein.

TABLE II

EFFECT OF UREA REACTOR PRODUCT (URP) ON LACTIC ACID CONTENT OF CORN SILAGE

| | % lactic acid[a] |
|---|---|
| Control (no additive) | 1.94 |
| URP[b,c] | 2.52 |

[a]Each value is the mean of two samples.
[b]URP was applied at 1.5% of the weight of the silage.
[c]Media was initially exposed to 60° C. for 4 hours and 55° C. for 2 hours, 12 hours later.

EXAMPLE 2

URP was added to aflatoxin contaminated whole corn grain at 6% of the weight of the corn. The corn grain was either dry (8.5% moisture by weight) or water was added to increase the moisture content to 20% moisture (by weight). Samples were stored in airtight glass containers, and the temperature was raised to 60° C. The temperature was maintained at 60° C. for 2 hours and then allowed to return to room temperature. After a 48 hour interval at room temperature, the process was repeated three more times so that a total of 8 hours was spent at a temperature of 60° C. The samples were then stored at room temperature for three weeks, ground and frozen until analysis for aflatoxin $B_1$ content. As shown in TABLE III, aflatoxin $B_1$ content was reduced to 35 ppb with dry corn and to less than 5 ppb (limit of detectability of procedure) for 20% moisture corn.

Aflatoxin is a mycotoxin produced by the mold aspergillus flavus and is very toxic to all animal species. The invention would be useful for preventing mold growth in grains in long-term storage programs by periodically releasing ammonia vapors. Also, if mold growth has occurred and aflatoxins are produced, detoxification would be possible. Currently the U.S. Food and Drug Administration does not allow grains containing more than 20 ppb to be shipped interstate or used in animal feeds. Therefore, this invention would be useful to recover the use of much of this grain.

TABLE III

EFFECT OF UREA REACTOR PRODUCT (URP) ON AFLATOXIN $B_1$, CONTENT OF WHOLE SHELLED CORN

| | Aflatoxin $B_1$, ppm | |
|---|---|---|
| Item | Dry corn | 20 moisture corn |
| Control[b] (no additive) | 375 ppb | 375 ppb |
| URP[b,c] | 35 ppb | less than 5 ppb |

[a]Each value is the mean of two samples.
[b]Temperature regime was 60° C. for 2 hours at 48 hour intervals and 4 intervals.
[c]URP was applied at 6% of the weight of the corn.

EXAMPLE 3

The effectiveness of ammonium carbamate as the source of ammonia for the treatment of high moisture coastal bermudagrass forage was demonstrated through an ammoniation study and a metabolism study.

Approximately five tons of high moisture bermudagrass hay (29% moisture by weight) was harvested in square bales and covered with plastic, such as shown in FIG. 1. URP (9.9% of the weight of the hay) was placed in 55 gallon drums with an electrical resistance heater coil under the drum. The temperature of the URP media was maintained at 60° C. for 7 days. Normally this type of high moisture forage would heat and mold within 2 weeks after storage. Approximately 30 days after ammoniation, the plastic cover was removed and the hay bales moved to a covered shed for storage until feeding. There were no visible signs of molding or heat damage to the hay.

Twelve yearling beef heifers (averaging 281 kg weight, initially) were placed on either dry control hay (15% moisture) or URP treated hay. Additionally, all heifers received 1% of their body weight as corn grain daily. As shown in TABLE IV, Heifers receiving the URP hay gained weight at a faster rate and tended to be more efficient in converting feed to weight gain.

TABLE IV

EFFECT OF UREA REACTOR PRODUCT (URP) TREATMENT OF BERMUDAGRASS HAY ON PERFORMANCE OF BEEF HEIFERS

| | Treatment[a] | |
|---|---|---|
| Item | Untreated Hay | URP Treated[b] Hay |
| Initial wt, kg | 281.5 | 279.9 |
| Final wt, kg | 349.7 | 361.0 |
| Total gain, kg | 68.2 | 81.1 |
| Average daily gain, kg | .81 | .97 |
| Feed/gain, kg | 6.0 | 5.4 |

[a]Each value is the mean of six animals.
[b]Hay was enclosed in polyethylene and treated with URP. URP was placed in steel drums and electrical resistance heat added (60° C. for 7 days).

It will be apparent to those skilled in the art that various modifications and variations can be made in the method of the present invention without departing from the scope or spirit of the invention. Thus, it is intended that the present invention covered the modifications and variations of this invention provided they come within the scope of the appended claims and their equivalents.

What is claimed is:

1. A method for treating organic farm material including one or more of hays, grains and silages, the method comprising the steps of:
(a) confining the organic farm material to a predetermined enclosure;
(b) introducing a solid chemical mixture into said enclosure;
(c) heating said solid chemical mixture to thereby release sufficient gaseous ammonia to said organic farm material to accomplish at least one of the following: prevent spoilage, reduce toxin levels, and improve fermentation of said organic farm material; and wherein:
said solid chemical mixture includes ammonium carbamate, ammonium hydroxide, urea, and water.

2. The method defined in claim 1, further including the step of:
rendering the predetermined enclosure substantially gas-tight.

3. The method defined in claim 2, wherein:
the step of confining the organic material to a predetermined enclosure includes covering the organic material with plastic and weighting the edges of the plastic to prevent gas from leaking from around the edges of the plastic.

4. The method defined in claim 1, wherein:
said solid chemical mixture includes in weight percentages, 57% ammonium carbamate, 14% ammonium hydroxide, 12% urea, and 17% water.

5. The method defined in claim 1, wherein:
the step of introducing the solid chemical mixture into the enclosure includes sprinkling discrete particles of the mixture onto the organic farm material as the organic farm material is being harvested in the field.

6. The method defined in claim 1, wherein:
the step of confining the organic farm material to a predetermined enclosure includes blowing the organic farm material up into a silo.

7. The method defined 6, wherein
the step of introducing the solid chemical mixture into the enclosure includes blowing discrete particles of the chemical mixture up into the silo as the organic farm material is blown up into, the silo.

8. The method defined in claim 1 wherein:
the step of confining the organic farm material to a predetermined enclosure includes placing the organic farm material into a pit dug into the ground and covering the pit with plastic which is weighted around the edges to substantially prevent leakage of gas from around the edges of the plastic.

9. The method defined in claim 1, wherein:
the step of confining the organic material to a predetermined enclosure includes the step of placing the organic material into a pit dug into the ground and letting the organic material at the top of the pit rot to seal itself.

10. The method defined in claim 1, wherein:
said heating step is carried out using a thermostatically controllable electrical resistance device.

11. The method defined in claim 10, wherein:
said ammonia is released to said organic farm material at a controlled release rate, said release rate being a function of the duration of activation of said electrical resistance device and the temperature of said electrical resistance device.

12. The method defined in claim 1, whereby: corn silage fermentation is enhanced.

13. The method defined in claim 1, whereby: aflatoxin levels in corn grain are reduced.

14. The method defined in claim 1, whereby:
heat damage and molding of high moisture forage are prevented.

15. A method for treating one or more of the group including harvested crops, animal feeds, feedgrains grains, and silages, the method comprising:

providing a solid chemical composition containing ammonium carbamate, ammonium hydroxide, urea, and water in the midst of the crops and feeds to be treated;

raising the temperature of said solid chemical composition to release gaseous ammonia;

controlling the temperature of said solid chemical composition to release sufficient gaseous ammonia to said crop or feed to accomplish at least one of the following: prevent spoilage, reduce toxin levels, and improve fermentation of said crop or feed.

* * * * *